United States Patent
Smits et al.

(10) Patent No.: US 6,544,190 B1
(45) Date of Patent: Apr. 8, 2003

(54) END TIDAL BREATH ANALYZER

(75) Inventors: Matthijs P. Smits, Sherwood, OR (US); Bryan P. Flaherty, Half Moon Bay, CA (US)

(73) Assignee: Natus Medical Inc., San Carlos, CA (US)

( * ) Notice: Subject to any disclaimer, the term of this patent is extended or adjusted under 35 U.S.C. 154(b) by 0 days.

(21) Appl. No.: 09/922,375

(22) Filed: Aug. 3, 2001

(51) Int. Cl.[7] .................................................. A61B 5/08
(52) U.S. Cl. ........................ 600/532; 600/529; 73/23.3
(58) Field of Search ............................... 600/529–538; 73/23.3

(56) References Cited

U.S. PATENT DOCUMENTS

| | | | |
|---|---|---|---|
| 4,387,722 A | * 6/1983 | Kearns | 600/529 |
| 5,293,875 A | * 3/1994 | Stone | 600/532 |
| 5,404,885 A | * 4/1995 | Sheehan et al. | 600/529 |
| 6,138,675 A | * 10/2000 | Berthon-Jones | 128/204.23 |

* cited by examiner

Primary Examiner—Robert L. Nasser
Assistant Examiner—Patricia Mallari
(74) Attorney, Agent, or Firm—Daniel P. Maguire

(57) ABSTRACT

A noninvasive apparatus and method for measuring a subject's end tidal carbon monoxide concentration is disclosed, featuring the ability to (i) determine carbon monoxide concentration on a breath-by-breath basis, (ii) determine mean carbon monoxide concentration by averaging local carbon monoxide values, (iii) avoid the premature determination that an end tidal phase is over, and (iv) determine when breath variability or system variability will likely preclude accurate testing. The disclosed device and method allow for more robust determination of end tidal carbon monoxide concentration in subjects with turbulent or irregular breath patterns.

35 Claims, 1 Drawing Sheet

END TIDAL BREATH ANALYZER

BACKGROUND OF THE INVENTION

1.) Field of the Invention

The present invention relates to devices and methods for measuring the breath concentration of carbon monoxide and other substances.

2.) Background of the Invention

There are many pathological conditions for which it would be clinically useful to measure the rate of hemolysis, or degradation of red blood cells, occurring within the body. These conditions include neonatal jaundice, anemia and many others. Exhaled carbon monoxide can be used as an index of the rate of hemolysis because carbon monoxide is formed when hemoglobin, which is contained in the red blood cell, is released from the red blood cell and broken down by enzymes.

The degradation of hemoglobin results in the equimolar formation of bilirubin and carbon monoxide. After formation, the carbon monoxide binds to hemoglobin within circulating red blood cells forming carboxyhemoglobin. The carboxyhemoglobin dissociates in the lung releasing carbon monoxide into the exhaled breath. The concentration of carbon monoxide present in the alveoli of the lungs is directly related to the concentration of carboxyhemoglobin within the blood.

Carbon monoxide is also present in the inhaled air as well, and this exogenous carbon monoxide will bind to hemoglobin to form carboxyhemoglobin in the lungs. In a steady state condition the difference between the inhaled concentration of carbon monoxide and the end tidal concentration will reflect the rate of hemolysis occurring within the body.

In many patients, including newborns, collection of end-tidal breath samples is difficult because the patient is unable to voluntarily control their breathing patterns to produce an end tidal sample.

One method of measuring end tidal carbon monoxide concentration from a non-cooperative patient is direct acquisition of an end tidal sample using a syringe or other suitable device, followed by analysis of the sample with gas chromatography or mass spectroscopy. Using this method, the clinician would observe the subject's chest movements to determine when end tidal breath was being exhaled. Thus, this method has the disadvantage of requiring a skilled clinician to take samples and to run the analysis.

Another method uses sensors to measure a subject's breath carbon monoxide concentration. This method, which is described in U.S. Pat. No. , 5,293,875, avoids the difficult task of inferring end tidal phases from chest movements, and avoids the need for gas chromatography or mass spectroscopy.

However, current electrochemical carbon monoxide sensors have relatively slow response times, so they cannot directly determine end tidal carbon monoxide concentrations. On the other hand, carbon dioxide sensors have relatively rapid response times, which allow for accurate measurements of end tidal carbon dioxide concentrations in normal-breathing humans. The '875 patent addresses the shortcoming of the carbon monoxide sensors, by exploiting the fact that end tidal carbon monoxide concentration (corrected to exclude the ambient concentration), is proportional to end tidal carbon dioxide concentration. Since it is possible to determine end tidal carbon dioxide concentration, it is also possible to calculate end tidal carbon monoxide concentration, by multiplying mean carbon monoxide concentration by the ratio of end tidal carbon dioxide concentration to mean carbon dioxide concentration. The '875 patent describes how to calculate end tidal carbon monoxide using this method.

A continuing challenge for the invention of the '875 patent is presented by irregular breath patterns, which are especially common in infants. Irregular breath patterns can make it difficult to determine the beginning and end of an end tidal phase, and can cause disassociations between carbon monoxide and carbon dioxide measurements due to the different sensor response times, and due to variations in the depth (shallow or deep) or timing of the subject's breathing.

The present invention marks an improvement over the method and apparatus of the '875 patent. More particularly, the present invention allows for more robust and accurate determination of end tidal carbon monoxide, by (i) determining carbon monoxide concentration on a breath-by-breath basis, (ii) improving the algorithm that detects when an end tidal phase is over, and (iii) rejecting test data whenever breath or system variability is so great as to likely impede accurate testing.

3.) BRIEF SUMMARY OF THE INVENTION

The present invention is an improved method and device for the detection of end tidal carbon monoxide concentration. Under the present invention, two sensors are used to gather data about the concentration of gases in the subject's exhaled breath. One sensor measures a first gas, preferably carbon dioxide, and the second measures carbon monoxide.

The present invention improves upon prior art end tidal carbon monoxide analyzers in three ways.

First, while the prior art only calculated an average end tidal carbon monoxide concentration over a period of time (time-based), the present invention calculates local or instantaneous end tidal carbon monoxide concentrations for each breath (breath-based). In order to calculate instantaneous end tidal carbon monoxide, the present invention uses a software filter that allows the carbon dioxide sensor to mimic the response characteristics of the carbon monoxide sensor.

Second, the improved device provides an end tidal carbon dioxide phase filter to avoid the premature determination that an end tidal phase has ended. The purpose of this filter is to help to avoid false peaks, which result from temporary spikes in a declining carbon dioxide concentration (inhale phase) that can be misinterpreted as the beginning of a new exhaled breath phase.

Third, the present invention provides a means to reject test data when excessive breath variability likely makes the test unreliable. Finally, the present invention provides a means to reject test data when system malfunctions and other problems cause excessive levels of system variability.

With these three improvements, the present invention provides a more robust and reliable evaluation of end tidal gas concentrations.

The present invention is especially useful for infants, who are prone to excessive levels of hemolysis and other conditions which result in high blood levels of carbon monoxide. However, the present invention can be used with subjects of all ages, and with many different exhaled gasses to diagnose or monitor a great variety of conditions.

4.) BRIEF DESCRIPTION OF THE DRAWINGS

5.) DETAILED DESCRIPTION

The present invention improves upon the apparatus and method disclosed by the '875 patent, and the '875 patent is incorporated by this reference into the disclosure of this patent. Because the hardware components of the present invention are described in the '875 patent, that disclosure is not repeated here. As explained in the '875 patent, the primary components of the end tidal breath analyzer are the gas sensors, the filters, the pump, the flow regulator, the sampling tube, and the tubing.

Figure 1:
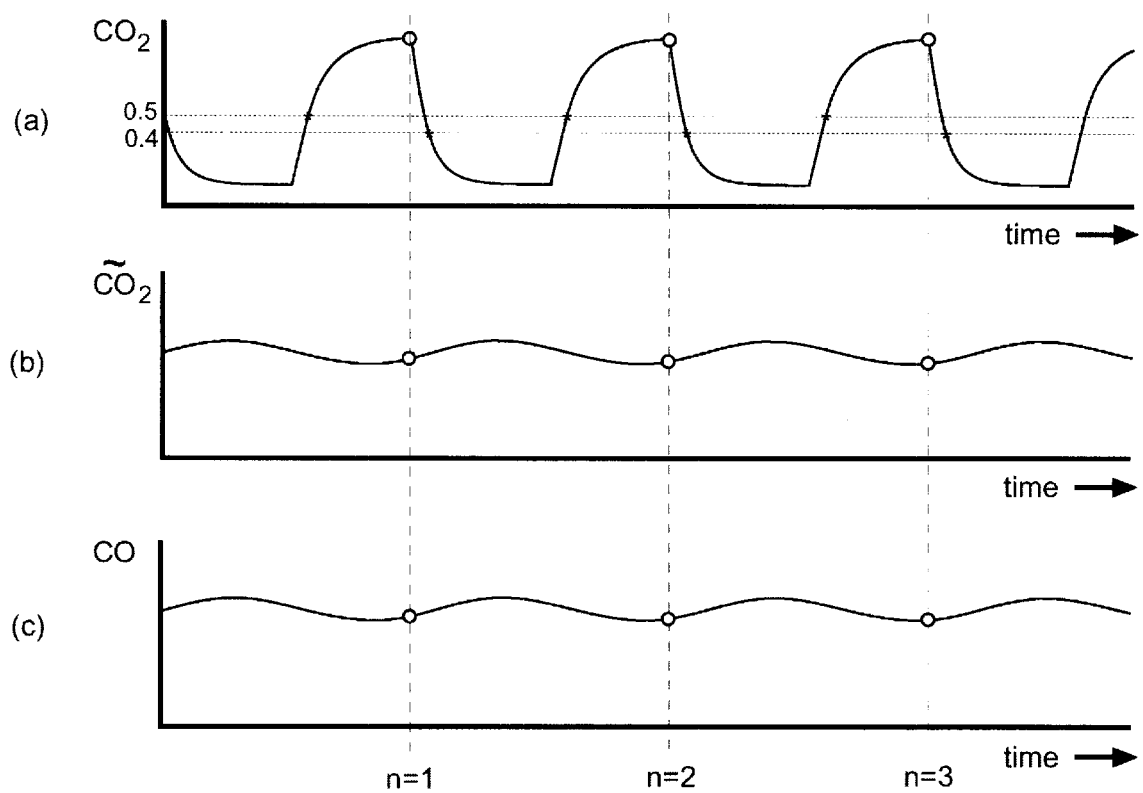
FIG. 1 shows the pattern of (a) carbon dioxide, (b) filtered carbon dioxide and (c) carbon monoxide levels over time in the breath of an adult with regular breath patterns.

The present invention has two gas sensors: one for detection of carbon monoxide, and another that detects a second gas that has an end tidal concentration proportional to carbon monoxide, preferably carbon dioxide. The two sensors have different response times. The carbon dioxide sensor has a relatively rapid response time, and can provide an accurate representation of end tidal phase concentration, as represented in FIG. 1a. The peaks in the graph represent the end tidal phases. In operation with the nasal tube assembly, the carbon dioxide sensor can be characterized as a first order system with a time constant of approximately 0.3 seconds. The carbon dioxide sensor samples at a rate of 30 Hz. The present invention can also be used with sensors for other gases diffused in blood, such as hydrogen.

Currently, state of the art carbon monoxide sensors have a relatively slow response time, and therefore cannot directly measure end tidal carbon monoxide concentration in subjects with normal breath rates. However, they can determine mean carbon monoxide concentration, as depicted in FIG. 1c. As explained in the '875 patent, end tidal carbon monoxide concentration can be calculated by multiplying mean carbon monoxide concentration by the ratio of end tidal to mean breath.

With every test, the output from the carbon monoxide sensor requires an initial period of time to settle. This settling is typically complete after 70 seconds, after which the carbon monoxide concentration is determined solely by the subject's breath. The carbon monoxide sensor can be characterized as a first-order system with a time constant of approximately 18 seconds, and a time delay of approximately 6 seconds. During breath measurement, the carbon monoxide sensor samples at a rate of 1 Hz.

In operation, the device takes carbon monoxide and carbon dioxide measurements after 70 seconds, the period of time necessary to clear any initial conditions. During the measurement period, the device calculates the end tidal carbon dioxide, $ETCO_2$, by determining the maximum carbon dioxide concentration during the testing period, and calculating an upper midline and a lower midline, according to the following formula:

$$CO_{2_{max}} = \max(CO_2)_{N_{BA}}$$

$$CO_{2_{uppermid}} = 0.5 * CO_{2_{max}}$$

$$CO_{2_{lowermid}} = 0.4 * CO_{2_{max}}$$

In these equations, $N_{BA}$ is the total number of samples in the breath analysis window, and $CO_{2_{max}}$ is the maximum carbon dioxide value in the breath analysis window.

The device considers the exhalation phase to begin with the first carbon dioxide reading above the upper midline, and to end with the first carbon dioxide concentration reading below the lower midline. FIG. 1a illustrates sample carbon dioxide measurements and the derived upper midline and lower midline. During the measurement period, the device determines the exhalation phase, using these midlines, and also using the end tidal phase filter described below. The peak of the exhalation phase is considered the end tidal phase.

In the past, the device would calculate the mean end tidal carbon dioxide concentration and the mean carbon dioxide concentration relative to the inhaled (ambient) carbon monoxide concentration over the entire measurement period, and then determine the ratio between the former and the latter, which is known as the duty cycle. In turn, the device would calculate the mean carbon monoxide concentration during the measurement period, and would multiply that value by the duty cycle to obtain the end tidal carbon monoxide concentration, corrected for inhaled carbon monoxide concentration (ETCOc).

However, in order to improve the performance of the device in the presence of irregular breath patterns, the present invention now calculates instantaneous or local carbon monoxide concentrations for each end tidal phase in the measurement window, and then takes a mean of the local ETCO measurements. These calculations are reflected in the following equation:

$$\mu ETCOc = \frac{1}{N} \sum_{n=1}^{N} \frac{ETCO_2(n)}{\tilde{C}O_2(n)} (CO(n) - \mu CO_{BG})$$

In this equation, $\mu ETCOc$ is the mean end tidal carbon monoxide concentration, measured in ppm, and corrected for background carbon monoxide. N is the total number of end tidal phases (breaths) within the measurement period. $ETCO_2$ is the end tidal carbon dioxide concentration, measured in ppm. $\tilde{C}O_2(n)$ represents the carbon dioxide concentration for the n-th end tidal phase, filtered so that the carbon dioxide signal mimics the response time and other characteristics of the carbon monoxide sensor, as explained below and in FIG. 1b. $CO(n)$ is the carbon monoxide concentration at end tidal phase n, and $\mu CO_{BG}$ is the mean background concentration of carbon monoxide. To obtain $\mu CO_{BG}$, a carbon monoxide reading is taken just after the measurement period. By subtracting out $\mu CO_{BG}$, the effects of ambient or inhaled carbon monoxide are eliminated. Inhaled carbon dioxide can also be measured and then subtracted from the measured carbon dioxide concentration.

As described in the above equation, whenever an $ETCO_2$ peak is located after 70 seconds into the measurement period, the corresponding CO and $\tilde{C}O_2$ signals are sampled, and a local ETCOc value is computed. After a minimum of 12 local ETCOc values are collected and a minimum of 20 seconds of carbon dioxide data are evaluated, the overall ETCOc is calculated by taking the mean of the local ETCOc values.

Alternatively, instead of taking the mean of the local ETCOc values, an overall ETCOc value could be determined by multiplying the average carbon monoxide concentration by the ratio of average end tidal carbon dioxide to the average filtered carbon dioxide concentration. However, the preferred method is to calculate local ETCOc values, so that the statistical analyses described below can be performed.

To determine the filtered carbon dioxide concentration, $\tilde{C}O_2$, the carbon monoxide sensor was modeled, including the associated "plumbing" or tubing between the two sensors. The plumbing can be characterized by a first-order low-pass filter with a time constant of 2 seconds, and a time delay of 3 seconds. The model for the carbon monoxide sensor is a first-order low-pass filter with a time constant of 18 seconds, and an additional time delay of 6 seconds. Both first-order filters are described in the following time domain equations and filter coefficients (sampling at 30 Hz):

$$\begin{cases} y(t) = \dfrac{b_1 x(t) + z(t-1)}{a_1} \\ z(t) = b_2 x(t) - a_2 y(t) \end{cases}$$

///
///

| Filtering Coefficient | Plumbing Filter | CO Sensor Filter |
|---|---|---|
| $a_1$ | 1 | 1 |
| $a_2$ | −9.834706949177776e-001 | −9.981498607113499e-001 |
| $b_1$ | 8.264652541111195e-003 | 9.250696443250384e-004 |
| $b_2$ | 8.264652541111195e-003 | 9.250696443250384e-004 |
| Initial Condition, $z_i$ | 2.5% | 2.5% |
| Added time delay, dt | 3 seconds | 3 seconds |

The resultant filtered carbon dioxide signal follows the response of the carbon monoxide sensor, as illustrated in FIGS. 1(b) and 1(c).

Because the carbon monoxide sensor samples at a much slower rate than the carbon dioxide sensor (1 Hz vs. 30 Hz), the carbon monoxide signal is linearly interpolated between samples to acquire the carbon monoxide sample at the same time as the end tidal carbon dioxide peak:

$$CO(n) = \frac{(t_{ETCO_2}(n) - t_1(n))}{t_2(n) - t_1(n)}(CO_{t_2}(n) - CO_{t_1}(n)) + CO_{t_1}(n)$$

In this equation, $CO_{t_1}$ and $CO_{t_2}$ represent the sampled carbon monoxide values (1 Hz rate) just before ($t_1$) and after ($t_2$) the end tidal carbon dioxide peak time $t_{ETCO_2}$.

Figure 2:
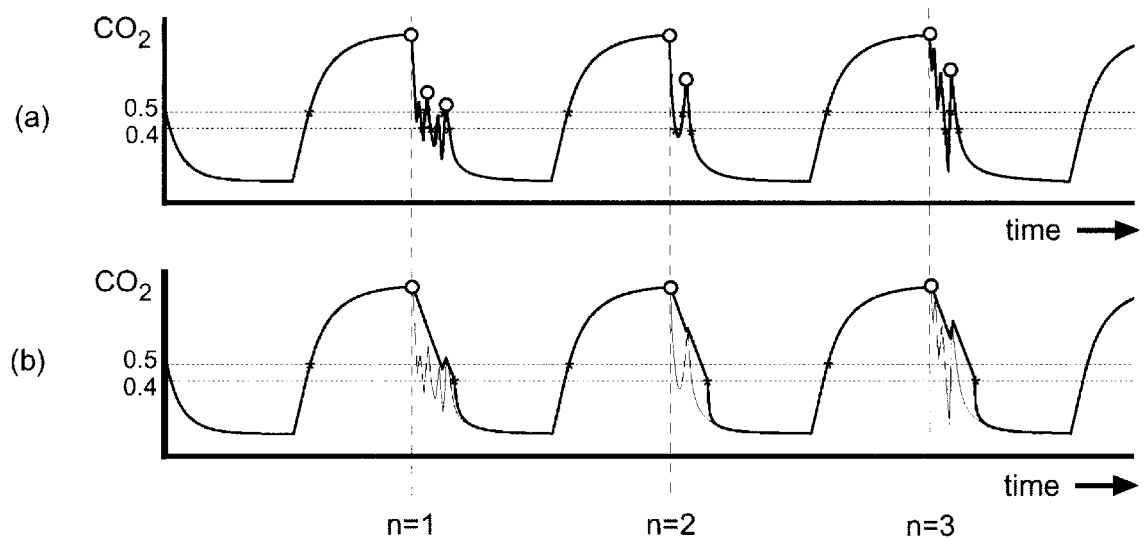
FIG. 2 shows (a) carbon dioxide levels over time in the breath of an adult with a turbulent inspired breath phase and (b) the same breath pattern with the end tidal phase filter.

Another aspect of the present invention is an end tidal phase filter, which helps to avoid the detection of false peaks or end tidal phases in subjects with turbulent breath patterns. Without this filter, the device can incorrectly interpret a sharp but transitory decline in carbon dioxide concentration as the completion of an end tidal phase. Having prematurely determined that the end tidal phase is over, the device might misinterpret a subsequent rise in carbon dioxide concentration as the start of a new end tidal phase. This phenomenon is illustrated in FIG. 2.

The end tidal phase filter is a software modification designed to address this problem. This filter is only used for peak end tidal carbon dioxide detection, and is only active during the exhaled breath phase. It operates by determining the average change in carbon dioxide concentration since the start of the end tidal breath phase, and limiting the reduction in carbon dioxide during the following inspired breath to this average. The filter is constructed as follows:

In these equations, $dV_{CO_2}$ represents the average change, sample to sample, in $CO_2$ since the start of the end tidal breath phase. $N_{ET}$ is the total number of carbon dioxide samples, up to the current position, in an end tidal phase. $V_{CO_2}$ is the output from the carbon dioxide sensor, in volts. $\tilde{V}_{CO_2}$ is the filtered output signal from the carbon dioxide sensor, during the end tidal phase. $n_{ET}$ is the carbon dioxide sample index, representing the number of end tidal samples. The phase filter employs a scale factor, k, which allows but does not require the rate of decrease of carbon dioxide to differ from the rate of increase in the same breath. The rate of increase in carbon dioxide is multiplied by the scale factor, and the decrease in carbon dioxide is limited to that product. Preferably, a scale factor of 1.4 is used, so that the rate of decrease can exceed the rate of increase by no more than 40%. The scale factor can be 1, which is the same as using no scale factor at all.

This filter only operates to limit the decline of carbon dioxide concentration, and does not limit the increase in carbon dioxide concentration, hence having no adverse effect on the measurement of end tidal carbon dioxide concentration. In addition, this filter design has shown to work properly for widely different breath rates.

The improved device also performs breath and system variability analysis, to determine if excessive irregular breath patterns or system-related problems are likely to prevent the device from accurately measuring carbon monoxide concentrations. Breath variability, caused by turbulent or excessive irregular breath patterns, can cause high variability in the calculated duty cycles, due to high variations in depth or timing of breath cycles. Likewise, malfunctions or significant differences between the carbon monoxide sensor model and the actual system performance can compromise test accuracy.

In conducting breath and system variability analysis, the present invention uses the performance benchmark, which accepts a difference in carbon monoxide concentrations between tests of no more than 0.3 ppm or 10%, whichever is greater. Put another way, under this benchmark, the maximum allowable error, $\epsilon$, is the greater of 0.3 ppm or 0.1 $\mu$CO.

This maximum allowable error can be decomposed into two equal-sized error boundaries:

$$\frac{2\sigma[ETCO_C]}{\sqrt{N_1}} \le \varepsilon \Rightarrow \begin{cases} \text{breath variability:} & \sigma\left[\dfrac{ETCO_2}{\tilde{C}O_2}\right]_N \mu CO \le \dfrac{\varepsilon}{2}\sqrt{N_1} \\ \text{system variability:} & \sigma\left[\dfrac{CO}{\tilde{C}O_2}\right]_N \mu ETCO_2 \le \dfrac{\varepsilon}{2}\sqrt{N_1} \end{cases}$$

In this equation, $N_1$ is the number of independent samples in the variability analysis window.

In performing the breath variability analysis, the device is designed so that test data is rejected if breath variability would cause half of the maximum allowable error, leaving room for system variability also up to half the maximum allowable error.

$$\begin{cases} dV_{CO_2}(N_{ET}) = \dfrac{k}{N_{ET}} \sum_{n_{ET}=1}^{N_{ET}} |V_{CO_2}(n_{ET}) - V_{CO_2}(n_{ET}-1)| \\ \tilde{V}_{CO_2}(n_{ET}) = \begin{cases} \tilde{V}_{CO_2}(n_{ET-1}) - dV_{CO_2}(n_{ET}) & V_{CO_2}(n_{ET}) < (\tilde{V}_{CO_2}(n_{ET-1}) - dV_{CO_2}(n_{ET})) \\ V_{CO_2}(n_{ET}) & \text{otherwise} \end{cases} \end{cases}$$

The improved device rejects the test data whenever the following breath variability threshold is not met:

$$\sigma\left[\frac{ETCO_2}{\tilde{C}O_2}\right]_N \leq \frac{\varepsilon}{2\mu CO}\sqrt{N_1}$$

In this equation, $N_1$, the number of independent samples, is approximately equal to N, the number of $ETCO_2$ peaks. Of course, different thresholds could be used.

As reflected in this equation, the device determines excessive breath variability based on the variation between independent samples of the ratio of end tidal carbon dioxide concentration and filtered carbon dioxide concentration. With regular breath patterns, the ratio between these two values should remain approximately constant. In subjects with irregular breath patterns, the ratio of end tidal breath to total breath changes over time.

Similar to the breath variability analysis, the system variability analysis compares carbon monoxide values with corresponding filtered carbon dioxide values, and rejects test data for measurement periods when the following test is not satisfied:

$$\sigma\left[\frac{CO}{\tilde{C}O_2}\right]_N \leq \frac{\varepsilon}{2\mu ETCO_2}\sqrt{N_1}$$

In this test, $N_1 = (t_N - t_1)^*I + 1$, where $N_1$ is the number of independent samples, $t_N - t_1$ is the time difference between the first and last $ETCO_2$ peak, and I is the independence factor, which is approximately equal to 0.05. The ratio between carbon monoxide concentrations and filtered carbon dioxide concentrations should be approximately constant, unless system problems are causing erroneous calculations of either of these values. Such system problems can be defined as any occurrence where the performance of the carbon monoxide sensor does not match the corresponding carbon monoxide sensor model as applied to the carbon dioxide signal.

The measurement period is initially set for 20 seconds. However, the measurement period is extended in five second increments anytime that (i) fewer than twelve breaths have been detected, (ii) the breath variability test fails, or (iii) the system variability tests fail. The measurement period can be extended a total of 120 seconds, until the total measurement period is 140 seconds.

Tests have shown that the new algorithm significantly improves the device's measurement accuracy in the presence of irregular breath patterns, as commonly observed in infants.

One skilled in the art will appreciate that the present invention can be practiced by other than the described embodiments, which are presented for purposes of illustration and not limitation. Although the present invention has been developed in the context of determining carbon monoxide concentrations, its method can be used in many fields, to derive information that is not directly measurable from a signal. Thus, the present invention can be used whenever two signals measure physical properties or conditions that are related or corresponded in a predictable way, such as the concentrations of carbon monoxide and carbon dioxide. By modeling a first signal to emulate or mimic the characteristics of a second related signal, information that is not directly measurable from the second signal can be determined, as described above in reference to carbon monoxide concentrations. It is believed that the modeling method described in this patent can be readily applied to any such situation, since the method does not depend on the nature of what is measured by the first and second signals. Thus, the modeling method of the present invention can be used to determine end tidal concentrations of any gas where there is no technology with a fast enough response time to directly measure end-tidal concentration. Examples of clinically relevant gases that could be measured are hydrogen (correlated with lactase deficiency and necrotizing enterocolitis), acetone (correlated with glycogen utilization and starvation), ethane (correlated with oxidative stress), nitric oxide (correlated with inflammatory response), and oxygen (correlated with metabolic rate abnormalities).

The modeling method of the present invention may have applications outside the context of end tidal breath analysis, such as in the optical analysis of pulsatile systems. For instance, the present invention might be useful in determining the pulsatile changes in capillary concentrations of substances that are detected only by weakly-penetrating wavelengths of light. The detection of such substances has been problematic in the past since the weakly-penetrating light requires long integration times for detection. More accurate detection of substances in pulsatile systems could result by relating the absorbance of the weakly-penetrating light to light wavelengths that readily penetrate, and therefore have a shorter integration time.

We claim:

1. An apparatus for determining a subject's end tidal carbon monoxide concentration, comprising:
    a first sensor, said first sensor generating a first output signal corresponding to the carbon monoxide concentration in said subject's breath;
    a second sensor, said second sensor generating a second output signal corresponding to the carbon dioxide concentration in said subject's breath;
    a microprocessor, said microprocessor receiving said first output signal and said second output signal, and having
        means for computing a plurality of local end tidal carbon monoxide concentrations based on said first and second output signals; and
        means for determining the subject's overall end tidal carbon monoxide concentration based on said local end tidal carbon monoxide concentrations.

2. An apparatus for determining the end tidal concentration of a gas in a subject's breath, comprising:
    a first sensor, said first sensor generating a first output signal corresponding to the concentration of a first gas in said subject's breath;
    a second sensor, said second sensor generating a second output signal corresponding to the concentration of a second gas in said subject's breath;
    a microprocessor, said microprocessor receiving said first output signal and said second output signal, and having
        means for computing a plurality of local end tidal concentrations of the first gas based on said first and second output signals; and
        means for determining the subject's overall concentration of the first gas based on said local end tidal concentrations of the first gas.

3. The apparatus according to claim 1 or 2, wherein said microprocessor additionally comprises means for filtering said second output signal to match the characteristics of said first output signal.

4. The apparatus according to claim 2, wherein said first gas is hydrogen.

5. A method for determining a subject's end tidal carbon monoxide concentration, comprising the steps of:

obtaining samples of the subject's breath;

taking carbon dioxide measurements and carbon monoxide measurements from said samples;

determining inhaled carbon monoxide levels from said carbon monoxide measurements, and excluding the effect of said inhaled carbon monoxide;

calculating local end tidal carbon monoxide measurements from the carbon dioxide measurements and the carbon monoxide measurements; and calculating the subject's overall end tidal carbon monoxide concentration from the local end tidal carbon monoxide concentrations.

6. A method for determining the concentration of a gas in a subject's end tidal breath, comprising the steps of:

obtaining samples of the subject's breath;

taking measurements of a first gas and a second gas from said samples;

determining inhaled levels of said first gas from said measurements of said first gas, and excluding the effect of said inhaled first gas;

calculating local end tidal concentrations of said first gas from said measurements of first gas and said second gas; and calculating the subject's overall concentration of said first gas from said local end tidal concentrations of said first gas.

7. A method for determining a subject's end tidal carbon monoxide concentration, comprising the steps of:

obtaining samples of the subject's breath;

obtaining a first output signal corresponding to the concentration of carbon monoxide in the subject's breath;

obtaining a second output signal corresponding to the concentration of carbon dioxide in the subject's breath;

determining inhaled carbon monoxide levels from said first output signal, and excluding the effect of said inhaled carbon monoxide;

calculating a carbon monoxide concentration from the first output signal;

calculating a local end tidal carbon dioxide concentration from the second output signal;

calculating a filtered carbon dioxide concentration from the second output signal;

calculating a local end tidal carbon monoxide concentration based on said local end tidal carbon dioxide concentration, said filtered carbon dioxide concentration, and said carbon monoxide concentration; and calculating said subject's overall end tidal carbon monoxide concentration from said local end tidal carbon monoxide concentration.

8. The method according to claim 7, wherein the step of calculating a filtered carbon dioxide concentration from said second output signal comprises the steps of:

filtering said second output signal to match the characteristics of said first output signal; and calculating carbon dioxide concentration from said filtered second output signal.

9. The method according to claim 7 or 8, wherein the step of calculating a local end tidal carbon monoxide concentration based on said local end tidal carbon dioxide concentration, said filtered carbon dioxide concentration, and said carbon monoxide concentration comprises multiplying the carbon monoxide concentration by the ratio of the local end tidal carbon dioxide concentration to the filtered carbon dioxide concentration.

10. A method for determining gas concentration in a subject, comprising the steps of:

obtaining samples of the subject's breath;

obtaining a first output signal corresponding to the concentration of a first gas in the subject's breath;

obtaining a second output signal corresponding to the concentration of a second gas in the subject's breath;

determining inhaled levels of said first gas from said first output signal, and excluding the effect of said inhaled first gas;

calculating a concentration of said first gas from the first output signal;

calculating a local end tidal concentration of said second gas from the second output signal;

calculating a filtered concentration of said second gas from the second output signal;

calculating a local end tidal concentration of said first gas based on said local end tidal concentration of said second gas, said filtered concentration of said second gas, and said concentration of said first gas; and calculating said subject's overall end tidal concentration of said first gas from said local end tidal concentration of said first gas.

11. The method according to claim 10, wherein the step of calculating a filtered concentration of said second gas from said second output signal comprises the steps of:

filtering said second output signal to match the characteristics of said first output signal; and calculating the concentration of said second gas from said filtered second output signal.

12. The method according to claim 10 or 11, wherein the step of calculating a local end tidal concentration of said first gas based on said local end tidal concentration of said second gas, said filtered concentration of said second gas, and said concentration of said first gas comprises multiplying the concentration of said first gas by the ratio of the local end tidal concentration of said second gas to the filtered concentration of said second gas.

13. A method for determining a subject's end tidal carbon monoxide concentration, comprising the steps of:

obtaining samples of the subject's breath;

obtaining a first output signal corresponding to the concentration of carbon monoxide in the subject's breath;

obtaining a second output signal corresponding to the concentration of an other gas in the subject's breath;

determining inhaled levels of carbon monoxide from said first output signal, and excluding the effect of said inhaled carbon monoxide;

determining that a subject has entered an exhalation phase based upon increases in the second output signal, and that a subject is ending an exhalation phase based upon decreases in the second output signal;

computing a corrected concentration of said other gas over time from said second output signal, by determining concentration of said other gas over time from said second signal, and by adjusting said concentration of said other gas over time so that the rate of reduction in concentration of said other gas during an exhalation phase is limited in proportion to the rate of increase during the same exhalation phase;

calculating a carbon monoxide concentration from the first output signal;

calculating a local end tidal concentration of said other gas from the second output signal;

calculating a local end tidal carbon monoxide concentration based on said local end tidal concentration of said other gas, said corrected concentration of said other gas, and said carbon monoxide concentration; and calculating said subject's overall end tidal carbon monoxide concentration from said local end tidal carbon monoxide concentrations.

14. The method according to claim 13, wherein said other gas is carbon dioxide.

15. An apparatus for determining a subject's end tidal carbon monoxide concentration, comprising:

a first sensor, said first sensor generating a first output signal corresponding to the carbon monoxide concentration in the subject's breath;

a second sensor, said second sensor generating a second output signal corresponding to the carbon dioxide concentration in the subject's breath;

a microprocessor, said microprocessor receiving said first output signal and said second output signal, and said microprocessor having means for excluding the effect of inhaled carbon monoxide;

means for determining carbon dioxide concentration over time from said second output signal;

means for determining end tidal breath phases based on peaks in said carbon dioxide concentration;

means for adjusting carbon dioxide concentration after said peaks so that any decrease in carbon dioxide concentration during an end tidal phase is limited in proportion to the rate of increase in the end tidal phase;

means for computing a plurality of local carbon monoxide concentrations based on said first output signal and said adjusted carbon dioxide concentration; and means for determining the subject's overall end tidal carbon monoxide concentration based on said local end tidal carbon monoxide concentrations.

16. An apparatus for determining a subject's end tidal carbon monoxide concentration, comprising:

a first sensor, said first sensor generating a first output signal corresponding to the carbon monoxide concentration in said subject's breath;

a second sensor, said second sensor generating a second output signal corresponding to the concentration of an other gas in said subject's breath;

a microprocessor, said microprocessor receiving said first output signal and said second output signal, and having means for excluding the effect of inhaled levels of the first gas;

means for determining a filtered concentration of said other gas and an end tidal concentration of said other gas;

means for determining excessive breath variability whenever the variation among a plurality of samples of the ratio between the end tidal concentration of said other gas to the concentration of the other gas exceeds a threshold;

means for computing a plurality of local end tidal carbon monoxide concentrations based on said first and second output signals; and means for determining the subject's overall end tidal carbon monoxide concentration based on said local end tidal carbon monoxide concentrations.

17. The apparatus according to claim 16, wherein the predetermined threshold is expressed in the formula, $$\sigma\left[\frac{ETg_2}{\tilde{g}_2}\right]_N \leq \frac{\varepsilon}{2\mu CO}\sqrt{N_1},$$

wherein $g_2$ represents the concentration of said other gas.

18. The apparatus according to claim 17, wherein said other gas is carbon dioxide.

19. A method for determining a subject's end tidal carbon monoxide concentration, comprising the steps of:

obtaining samples of the subject's breath;

obtaining a first output signal corresponding to the concentration of carbon monoxide in the subject's breath;

obtaining a second output signal corresponding to the concentration of an other gas in the subject's breath;

determining inhaled levels of carbon monoxide from said first output signal, and excluding the effect of said inhaled carbon monoxide;

calculating a carbon monoxide concentration from the first output signal;

calculating a local end tidal concentration of said other gas from the second output signal;

calculating a filtered concentration of said other gas from the second output signal;

determining excessive breath variability whenever the variation among a plurality of samples of the ratio between the end tidal concentration of said other gas to the filtered concentration of said other gas exceeds a predetermined threshold;

computing a plurality of local end tidal carbon monoxide concentrations based on said first and second.output signals; and calculating said subject's overall end tidal carbon monoxide concentration from said local end tidal carbon monoxide concentrations.

20. The method according to claim 19, wherein the predetermined threshold is expressed in the formula:

$$\sigma\left[\frac{ETg_2}{\tilde{g}_2}\right]_N \leq \frac{\varepsilon}{2\mu CO}\sqrt{N_1},$$

wherein $g_2$ represents the concentration of said other gas.

21. The method according to claim 20, wherein said other gas is carbon dioxide.

22. A method for determining gas concentration in a subject, comprising the steps of:

obtaining samples of the subject's breath;

obtaining a first output signal corresponding to the concentration of a first gas in the subject's breath;

obtaining a second output signal corresponding to the concentration of a second gas in the subject's breath;

determining inhaled levels of said first gas from said first output signal, and excluding the effect of said inhaled first gas;

calculating a concentration of said first gas from the first output signal;

calculating a local end tidal concentration of said second gas from the second output signal;

calculating a mean concentration of said second gas;

determining excessive breath variability whenever the variation among a plurality of samples of the ratio between the end tidal concentration of said second gas to the mean concentration of said second gas exceeds a predetermined threshold; and calculating said subject's overall end tidal concentration of said first gas based on said first and second output signals.

23. A method for determining whether variability in a subject's breathing patterns will preclude accurate breath analysis, comprising the steps of:

obtaining a sample of the subject's breath for the purpose of chemical analysis of said breath;

measuring the subject's breathing patterns;

determining excessive breath variability whenever the variation in the subject's breathing patterns over a period of time exceeds a threshold, and to the extent that excessive breath variability has not been found, analyzing the contents of the subject's breath.

24. An apparatus for determining a subject's end tidal carbon monoxide concentration, comprising:

a first sensor, said first sensor generating a first output signal corresponding to the carbon monoxide concentration in said subject's breath;

a second sensor, said second sensor generating a second output signal corresponding to the concentration of an other gas in said subject's breath;

a microprocessor, said microprocessor receiving said first output signal and said second output signal, and having:

means for excluding the effect of inhaled carbon monoxide;

means for determining a filtered concentration of said other gas and an end tidal concentration of said other gas;

means for determining excessive system variability whenever the variation among a plurality of samples of the ratio between the carbon monoxide concentration and the filtered concentration of said other gas exceeds a predetermined threshold;

means for computing a plurality of local end tidal carbon monoxide concentrations based on said first output signal and said second output signal; and means for determining the subject's overall end tidal carbon monoxide concentration based on said local end tidal carbon monoxide concentrations.

25. The apparatus according to claim 24, wherein the predetermined threshold is expressed in the formula:

$$\sigma\left[\frac{CO}{\bar{g}_2}\right]_N \leq \frac{\varepsilon}{2\mu ET g_2}\sqrt{N_1},$$

wherein $g_2$ represents the concentration of said other gas.

26. The apparatus according to claim 25, wherein said other gas is carbon dioxide.

27. A method for determining a subject's end tidal carbon monoxide concentration, comprising the steps of:

obtaining samples of the subject's breath;

obtaining a first output signal corresponding to the concentration of carbon monoxide in the subject's breath;

obtaining a second output signal corresponding to the concentration of an other gas in the subject's breath;

determining inhaled levels of carbon monoxide from said first output signal, and excluding the effect of said inhaled carbon monoxide;

calculating a carbon monoxide concentration from the first output signal;

calculating a local end tidal concentration of said other gas from the second output signal;

calculating a filtered concentration of said other gas from the second output signal;

determining excessive system variability whenever the variation among a plurality of samples of the ratio between the carbon monoxide concentration and the filtered concentration of said other gas exceeds a predetermined threshold;

computing a plurality of local end tidal carbon monoxide concentrations based on said first and second output signals; and calculating said subject's overall end tidal carbon monoxide concentration from said local end tidal carbon monoxide concentrations.

28. The method according to claim 27, wherein the predetermined threshold is expressed in the formula:

$$\sigma\left[\frac{CO}{\bar{g}_2}\right]_N \leq \frac{\varepsilon}{2\mu ET g_2}\sqrt{N_1},$$

wherein $g_2$ represents the concentration of said other gas.

29. The method according to claim 28, wherein said other gas is carbon dioxide.

30. A method for determining a subject's end tidal carbon monoxide concentration, comprising the steps of:

obtaining samples of the subject's breath;

obtaining a first output signal corresponding to the concentration of carbon monoxide in the subject's breath;

obtaining a second output signal corresponding to the concentration of an other gas in the subject's breath;

determining inhaled levels of carbon monoxide from said first output signal, and excluding the effect of said inhaled carbon monoxide;

calculating a carbon monoxide concentration from the first output signal;

calculating a local end tidal concentration of said other gas from the second output signal;

calculating a filtered concentration of said other gas from the second output signal;

determining excessive system variability whenever the variation among a plurality of samples of the ratio between the carbon monoxide concentration and the filtered concentration of said other gas exceeds a predetermined threshold; and calculating said subject's overall end tidal carbon monoxide concentration based on said first and second output signals.

31. A method for determining a subject's end tidal carbon monoxide concentration, comprising the steps of:

obtaining samples of the subject's breath;

obtaining a first output signal corresponding to the concentration of carbon monoxide in the subject's breath;

obtaining a second output signal corresponding to the concentration of carbon dioxide in the subject's breath;

determining inhaled levels of carbon monoxide from said first output signal, and excluding the effect of said inhaled carbon monoxide;

calculating a carbon monoxide concentration from the first output signal;

calculating a local end tidal carbon dioxide concentration from the second output signal;

calculating a filtered carbon dioxide concentration from the second output signal; and calculating said subject's overall end tidal carbon monoxide concentration from said local end tidal carbon dioxide concentration, said filtered carbon dioxide concentration, and said carbon monoxide concentration.

32. A method for determining the concentration of a first bodily substance by using the concentration of a corresponding second bodily substance, comprising the steps of:

using a first sensor to obtain a first output signal corresponding to the concentration of the first substance;

using a second sensor to obtain a second output signal corresponding to the concentration of the second substance, said second sensor having a faster response time than said first sensor;

calculating a local concentration of the second substance from the second output signal;

calculating a concentration of the first substance from the first output signal;

creating a filtered second output signal by filtering said second output signal to match the characteristics of said first output signal;

calculating a filtered concentration of said second substance from said filtered second output signal calculating a local concentration of said first substance based on said concentration of said second substance, said filtered concentration of said second substance, and said concentration of said first substance.

33. An apparatus for determining the concentration of a gas in a subject's breath, comprising:

a first sensor, said first sensor generating a first output signal corresponding to the concentration of a first gas in said subject's breath;

a second sensor, said second sensor generating a second output signal corresponding to the concentration of a second gas in said subject's breath;

a microprocessor, said microprocessor receiving said first output signal and said second output signal, and having means for filtering said second output signal to match the characteristics of said first output signal;

means for computing concentration of the first gas based on said first and second output signals.

34. The apparatus according to claim 33, wherein said first gas is carbon monoxide.

35. The apparatus according to claim 34, wherein said second gas is carbon dioxide.

* * * * *